(12) United States Patent
Tomatis (10) Patent No.: US 6,852,343 B2
(45) Date of Patent: Feb. 8, 2005

(54) ANTIADIPOSE TOPICAL TREATMENT COMPOSITION BASED ON GARLIC BULBS EXTRACTS, AND COSMETIC AND THERAPEUTIC USES

(75) Inventor: Isabelle Tomatis, Tournefeuille (FR)

(73) Assignee: Pierre Fabre Dermo-Cosmetique, Boulogne (FR)

( * ) Notice: Subject to any disclaimer, the term of this patent is extended or adjusted under 35 U.S.C. 154(b) by 14 days.

(21) Appl. No.: 09/984,037

(22) Filed: Oct. 26, 2001

(65) Prior Publication Data

US 2002/0146474 A1 Oct. 10, 2002

(30) Foreign Application Priority Data

Oct. 31, 2000 (FR) .............................. 00 13973

(51) Int. Cl.⁷ .............................. A61K 35/78
(52) U.S. Cl. .................. 424/754; 424/725; 514/860
(58) Field of Search ................ 424/754, 725, 424/401, 78.03; 514/860

(56) References Cited

FOREIGN PATENT DOCUMENTS

| EP | 0 333 548 A1 | 9/1989 |
| EP | 0 923 937 A2 | 6/1999 |
| FR | NF T 75-006 | 2/1998 |
| FR | 2 804 319 A1 | 8/2001 |
| GB | 1106551 | 3/1968 |
| JP | 4338336 | 11/1992 |

OTHER PUBLICATIONS

S. Klaus, "Functional Differentiation of White and Brown Adipocytes", RG 002, Bio Essays, vol. 19, No. 3, pp. 215–223, Dec. 23, 1996.
S. Farmer et al., "Insights Into the Transcriptional Control of Adipocyte Differentiation", RG 005, Journal of Cellular Biochemistry Supplements, 32/33, pp. 59–67, 1999.
M.D. Lane et al., "Regulated Expression of the Obese Product (leptin) in White Adipose Tissue and 3T3–L1 Adipocytes", Proc. Natl. Acad. Sci. USA, vol. 92, pp 9034–9037, Sep. 1995.
J. N. Dhuley et al., "Hypolipidaemic and Antioxidant Activity of Diallyl Disulfide in Rats", Royal Pharmaceutical Society of Great Britain, 1999 XP–002173644, Abstract only.
Derwent Publications Ltd., London, GB, AN 2000–489113, XP–002173645 & KP 99 055 308 A (LG CHEM), Jul. 15, 1999.

*Primary Examiner*—Sreeni Padmanabhan
*Assistant Examiner*—Gina C. Yu
(74) *Attorney, Agent, or Firm*—Young & Thompson (57) ABSTRACT

The invention relates to an antiadipose topical treatment composition comprising an effective amount of at least one antiadipose active agent chosen from extracts of *Allium sativum* bulbs, with the exception of an oleoresin extracted with hexane, and a cosmetically or pharmaceutically acceptable excipient which is suitable for topical application for external use—especially on the skin. The invention covers the uses of this composition and of its extracts cosmetically for treating cellulite and localized dermal excess adipose, and therapeutically for treating obesity.

3 Claims, 2 Drawing Sheets

SEQUENCE LISTING

<160> NUMBER OF SEQ ID NOS: 4

<210> SEQ ID NO 1
<211> LENGTH: 23
<212> TYPE: DNA
<213> ORGANISM: Mus musculus

<400> SEQUENCE: 1
tgttgaccca gagcatggtg cct          23

<210> SEQ ID NO 2
<211> LENGTH: 23
<212> TYPE: DNA
<213> ORGANISM: Mus musculus

<400> SEQUENCE: 2
caggttctac tttgatcgca ctt          23

<210> SEQ ID NO 3
<211> LENGTH: 19
<212> TYPE: DNA
<213> ORGANISM: Homo sapiens

<400> SEQUENCE: 3
gcgattcctt cactgatac          19

<210> SEQ ID NO 4
<211> LENGTH: 20
<212> TYPE: DNA

-continued

```
<213> ORGANISM: Homo sapiens

<400> SEQUENCE: 4
gcattatgag acatccccac                                              20
```

ANTIADIPOSE TOPICAL TREATMENT COMPOSITION BASED ON GARLIC BULBS EXTRACTS, AND COSMETIC AND THERAPEUTIC USES

The invention relates to an antiadipose topical treatment composition and to the uses of this composition and/or of garlic bulbs extracts cosmetically for preventively or curatively treating cellulite and localized dermal excess adipose, or therapeutically for treating obesity.

More than 90% of women have cellulite to a greater or lesser degree. There are many causes of cellulite: genetic predispositions, hormonal imbalance, dietetic errors, circulatory problems, stress or depression. In brief outline, cellulite corresponds to an increase in adipose tissue in certain regions of the body, in particular on the hips, the buttocks, the knees and the forearms. This adipose tissue or fatty mass of the body is present below virtually the entire surface of the skin. Cellulite is often associated with an overall excess of adipose and the stability of the fatty mass is an important point in controlling the development of cellulite.

Cellulite is localized in the dermis. In the hypodermis, a deep layer of the dermis, the adipose cells, or adipocytes, gather together to form lobules delimited by partitions (rows of collagen fibers) that are parallel to each other and perpendicular to the skin surface. The adipocyte is a large cell, 80% of the volume of which consists of one or more lipid vacuoles. It is of variable size. If the vacuole is overloaded with fat, the volume of the adipocyte increases and the dermal connective tissue thickens.

Cellulite also depends on functional criteria, since it is also a localized mass, associated with an insufficiency of the venous tonus and/or an impairment of the lymphatic system.

The first deformation of cellulitic tissue takes place in the adipocytes. As soon as the volume of the adipocytes increases, the partitions undergo a deep stretching which appears at the surface of the epidermis in the form of depressions in certain places. These depressions are all the more visible if the skin is pinched: this is known as the orange-peel effect.

The second deformation takes place in the ground substance. The ground substance changes according to the amount of water it retains. This explains the loss of suppleness of the skin in cellulitic areas. The pressure of the water retained by the ground substance squashes the cells and thereby results in degradation of the elastin and collagen fibers.

Lastly, the final consequence of the excessive water retention in the ground substance is a compression of the lymphatic and blood vessels. The consequence of this compression is to reduce the venous blood flow and the flow of lymph, which is experienced at both the epidermal and hypodermal levels. This results in poor blood equilibrium and a deficient removal of toxins and waste.

From a metabolic point of view, in adipose tissue, the adipocyte functions as an energy reserve for the body.

To ensure its function as an energy reserve, the adipocyte is capable of storing energy in the form of triglycerides in its lipid droplets (this is lipogenesis) and then of releasing this energy in the form of fatty acids into the blood circulation (this is lipolysis).

It is the equilibrium between these two metabolic routes (lipogenesis and lipolysis) which conditions adiposity.

The lipogenic function of the adipocyte necessitates the presence of fatty acids essentially derived from triglyceride-rich circulating lipoproteins.

On the catabolic side, lipolysis corresponds to the separation of the constituents of the adipocyte triglycerides into glycerol, on the one hand, and fatty acids, on the other hand. This lipolysis takes place due to the action of a limiting enzyme, hormone-sensitive lipase. The activation of hormone-sensitive lipase depends on the content of cyclic AMP. In human adipose tissue, the hormones and various agents are capable of modulating the intracellular concentrations of cAMP, and thus participate in controlling hormone-sensitive lipase and therefore lipolysis.

At the present time, all known slimming creams contain a mixture of at least one active agent which promotes lipolysis and/or inhibits lipogenesis and/or which attempts to restore the lymphatic and capillary microcirculation.

However, despite the diversity of the slimming creams developed to date and the large number of related therapies proposed in the treatment of cellulite (electrical stimulation, heat, massaging, etc.), no treatment has been found to be truly effective for combating cellulite.

In parallel, the mechanisms involved in the expansion of the fatty mass have been elucidated in recent years.

The excessive development of adipose mass is usually associated with an increase in the volume of the adipocytes, and in their triglyceride content, without there being an increase in their number: this is known as hypertrophy. In certain cases of excess weight, hypertrophy is accompanied by hyperplasia, that is to say an increase in the number of adipose cells.

It has also now been demonstrated that the number of fat cells is not determined during the perinatal period, since the formation of adipocytes may take place throughout life. It arises from precursor cells, the preadipocytes. The preadipocyte is a thin cell of fibroblast morphology: it is this cell, and not the adipocyte, which is capable of multiplying.

In brief outline, the terminal adipocyte differentiation takes place in two steps with conversion of the preadipocyte into mature adipocyte, the latter being capable of accumulating triglycerides.

However, although such findings offer a novel and interesting approach in the treatment of cellulite, they have not resulted in any practical action owing to the inability to find active principles making it possible to achieve, by topical application, an inhibition of the adipocytic conversion of the preadipocytes into mature adipocytes.

The present invention is directed toward redressing this absence, and its main object is to provide a therapeutic or cosmetic composition for antiadipose treatment by topical application for external use (on the skin), which especially acts very effectively in blocking the differentiation of preadipocytes into adipocytes.

More particularly, the invention is directed toward proposing an improved cosmetic or therapeutic treatment of cellulite, localized dermal excess adipose, and obesity.

The invention is moreover directed toward proposing novel cosmetic or therapeutic uses of extracts—especially nonaqueous extracts—of bulbs of *Allium sativum* (garlic).

In the whole text, the term "bulbs" should be understood as embracing just as well actual bulbs of the plant (groups of garlic cloves), as separated garlic cloves.

The invention is also directed toward proposing novel compositions based on garlic bulb extracts and their uses, especially for cosmetic or therapeutic purposes.

Another object of the invention is to provide a therapeutic composition acting on mature hypertrophied adipocytes in the context of treating obesity.

Throughout the text hereinbelow, the terms defining the extracts (extract, essential oil, absolute, concrete, oleoresin, etc.) are used according to the terminology defined by standard NF T 75-006 (February 1998).

The invention thus relates to a topical treatment composition for external use, wherein it consists:

of an effective amount of at least one antiadipose active agent chosen from extracts of Allium sativum bulbs, with the exception of an oleoresin extracted with hexane, optionally, of one or more other additional active agents, with the exception of Nymphaceae extracts, of a cosmetically or pharmaceutically acceptable excipient which is suitable for topical application for external use—especially on the skin.

Advantageously, the composition according to the invention comprises an amount of at least one antiadipose active agent which is suitable for at least substantially inhibiting the differentiation of preadipocytes into mature adipocytes, without substantially causing any skin irritation or sensitization.

Advantageously and according to the invention, the composition comprises an effective amount of at least one antiadipose active agent chosen from nonaqueous extracts of Allium sativum bulbs.

Advantageously and according to the invention, the amount of extract(s) of Allium sativum bulbs is between 3 ppm and 20 ppm—especially of the order of 10 ppm—.

In a first embodiment, and according to the invention, the composition comprises, as antiadipose active agent, an essential oil of Allium sativum bulbs and an emulsifier.

Moreover, in order to prepare a cream which may be applied topically, and advantageously, the essential oil/emulsifier mixture is incorporated into a gel and a liquid excipient such as water.

In a second embodiment, and according to the invention, the composition comprises, as antiadipose active agent, at least one absolute of Allium sativum bulbs in aqueous solution. Advantageously and according to the invention, it comprises at least one absolute obtained from a concrete extracted from Allium sativum bulbs. Advantageously and according to the invention, it also comprises at least one absolute obtained from an oleoresin extracted from Allium sativum bulbs.

More particularly, a feature of a composition according to the invention is that it advantageously comprises, as antiadipose active agent, at least one extract of Allium sativum bulbs chosen from an essential oil, an absolute obtained from a concrete extracted with hexane, an absolute obtained from a concrete extracted with ethyl acetate, and an absolute obtained from an oleoresin extracted with acetone.

According to the invention, for a composition comprising an absolute obtained from a concrete extracted with hexane, the amount of the absolute is advantageously between 3 ppm and 20 ppm—especially of the order of 10 ppm—.

According to the invention, for a composition comprising at least one extract of Allium sativum bulbs chosen from an essential oil, an absolute obtained from a concrete extracted with ethylacetate, an absolute obtained from an oleoresin extracted with acetone, the amount of extract(s) is advantageously between 5 ppm and 20 ppm—especially of the order of 10 ppm—.

It should be noted that in the practice of the present invention, the different absolutes are diluted at 25% in ethanol. However, the proportion of absolute(s) in the different compositions according to the invention refer to an amount of "pure" absolute(s) that wants to say (an) absolute (s) containing less than 2% of ethanol.

The invention is thus based on the very surprising and unexpected discovery that extracts of Allium sativum bulbs show very efficient activity in blocking the differentiation of adipose cells.

It should be noted that Allium sativum has been renowned for many centuries for having antiseptic, antiviral, cardioprotective, tonic, diuretic, etc. activity.

EP-0 923 937 describes a composition for treating skin disorders such as allergies, depigmentations, mycoses, chapping, hyperkeratoses, cuts and burns, comprising at least two plant extracts in the form of oil or powder, obtained by extraction with solvents using dried plants.

These are thus oleoresins (or resinoids). Among the various extracts, the composition comprises 1 to 3% of a garlic oleoresin extracted with hexane, which shows no antiadipose activity.

GB-1 106 551 describes the use of extracts of plants of the Nymphaceae family as active agents for the therapeutic treatment of neoplasms and cellulite. The compositions described also include one or more additional essential oil(s) of plants of other species, especially of the Cruciferaceae family (for example mustard oil or horseradish oil) or of the Liliaceae family (for example garlic oil), producing a stabilizing effect on Nymphaceae extracts, and a synergistic effect with these extracts. For the topical treatment of cellulite, the essential oils ire dissolved in olive oil. Said document indicates that said additional essential oils have no intrinsic effect individually.

EP-0-333 548 describes stable aqueous emulsions of essential oil of orange comprising 1 to 45 parts by weight of essential oil; 0.01 to 1 part by weight of a nonionic emulsifier chosen from sucroglycerides and sucroesters; 0.2 to 1.5 parts by weight of xanthan gum, and the remainder by weight of water. These emulsions may be used to prepare concentrates for flavouring food products, especially alcohol-free drinks and candy or concentrates for cosmetics. Said document indicates that, in principle, any plant "oil" (in fact any extract) can be used in the emulsion, and thus mentions among them especially "garlic oil". Nevertheless, it gives embodiments only in the case of orange oil. However, with the proportions indicated, a stable emulsion of essential oil cannot be obtained with all the known essential oils, and in particular with essential oil of garlic. Said document therefore does not provide any realistic teaching relating to a composition based on essential oil of garlic.

JP-04 338 336 describes tablets for the oral treatment of obesity, comprising garlic extracts obtained from dried garlic and from an extraction with water or ethanol. Said document is thus directed toward exploiting the well-known hypolipidemic effect of certain garlic extracts in the circulating blood.

FR-2 804 319, published on Aug. 3, 2001 describes a cosmetic slimming composition comprising a plant extract containing ANP, which is necessarily obtained by extraction with water and using the stems, leaves and petals of the plants. Said document mentions various plants which may be used, including garlic, but does not describe a composition comprising an extract of *Allium sativum* bulbs. The mechanism of action of the composition consists in promoting the lipolysis of the adipocytes, but does not in any way-act on converting the preadipocytes into mature adipocytes.

Thus, there was nothing in the current knowledge to lead one to expect that the use of extracts of *Allium sativum* bulbs might lead to the emergence of a new generation of slimming creams acting no longer only on the mechanisms for storing/destocking fats (and thus on lipogenesis/lipolysis), but especially on the process of differentiation of preadipocytes into mature adipocytes.

The *Allium sativum* extracts according to the invention act locally on the adipose cell without causing the release into the blood circulation of some of its fatty acids which, owing to them not having been burnt off, might turn out to be detrimental in terms of health (deposition on the arterial wall or the intra-abdominal tissue).

Thus, the *Allium sativum* extracts according to the invention act via a novel approach for combating cellulite: by limiting the recruitment of dormant preadipocytes, they limit the expansion of the adipose tissue.

However, this is not their only efficacy, since it has been found that with only one antiadipose active agent according to the invention, several keys for combating cellulite are provided. This is because an antiadipose agent according to the invention also ensures good vascularization of adipose tissue by reducing the levels of vasopressors.

The *Allium sativum* extracts according to the invention thus constitute antiadipose active agents with maximum efficacy, making it unnecessary to multiply the combinations of active agents in cosmetic or therapeutic slimming formulations.

Other experiments have also made it possible to observe, unexpectedly, that the antiadipose active agents according to the invention are also active on mature hypertrophied adipocytes. They thus act on the two processes of adipose growth, hyperplasia and hypertrophy, which allows them to be used successfully in the therapeutic field for treating obesity.

Another observed advantage of the antiadipose active agents according to the invention lies in the fact that the phenomena obtained are reversible and that, consequently, they do not lead to a blocking of the physiological mechanism.

Moreover, since the efficacy of the antiadipose active agents according to the invention is based especially on reducing the recruitment of dormant preadipocytes, the therapeutic or cosmetic compositions according to the invention constitute a bodycare therapy which, preferentially, is applied as an external treatment to the areas of skin to be treated at least once a day, every day of the year.

In this case, the composition according to the invention does not require any active agent other than the one according to the invention, and the *Allium sativum* extract(s) may thus constitute the only antiadipose active agent(s) in said composition. Consequently, the composition according to the invention is free of an additional active agent. In particular, preferably, the extract(s) of *Allium sativum* bulbs is (are) the only plant extract(s) in a composition according to the invention.

However, a composition according to the invention may also be used for "flash" treatments consisting in carrying out a treatment lasting two or three months, especially before the summer period. In this case, it advantageously comprises an additional active agent consisting of a lipolytic agent of any type known per se. Advantageously, a composition according to the invention comprises at least one lipolytic agent chosen from lipolytic agents of natural origin (such as caffeine and lipolytic agents) or of synthetic origin (compounds) of xanthine bases), capable of stimulating the synthesis of cAMP.

Other additional active agents, especially with a cosmetic effect, may be combined with the antiadipose active agents according to the invention. A composition according to the invention may contain a certain number of agents capable of: stabilizing the elastic network (for example silicon derivatives); and/or affording an immediate tensioning effect (incorporation of synthetic polymers or plant proteins (from soya or wheat germ)); and/or ensuring an optimum hydration (incorporation of wetting agents and/or restructuring agents).

Advantageously, a composition according to the invention does not require the incorporation of agents capable of improving its penetration power (such as exfoliants).

Similarly, it is not necessary to incorporate into a composition according to the invention agents capable of improving the microcirculation of the skin.

The composition according to the invention may comprise any pharmaceutically or cosmetically acceptable excipient, which is compatible with the antiadipose active agents according to the invention, and which may comprise any suitable adjuvant, including gelling agents, fragrances, preserving agents, stabilizers, colorants, etc. for obtaining the desired and suitable pharmaceutical form. A composition according to the invention may, for example, be free of xanthan gum.

In the case of an essential oil of *Allium sativum* bulbs, it is especially possible to use as emulsifier the product known as Liposol sold by the company Siegen (Geneva, Switzerland), or any other emulsifier, especially any emulsifier which is neither a sucroglyceride nor a sucroester.

The amount of emulsifier used is adapted to obtain the desired emulsion. In practice, it is very much larger—typically 50 times—than that of essential oil.

In the case of an absolute in aqueous solution, the composition according to the invention is advantageously in the form of a simple lotion.

Examples of the preparation of a composition according to the invention are as follows.

For the preparation of a cream for topical application, the essential oil of *Allium sativum* is first incorporated into an emulsifier such as Liposol (Siegen, Switzerland), the respective proportions by volume being, for example, of the order of 0.001% essential oil, 0.05% Liposol and the remainder to 100% of excipient.

Lotions may be prepared, for example, with the absolutes. As examples, the amounts, as concentrations by volume, of the various constituents may be as follows:

Composition No. 1:
Absolute of *Allium sativum* bulbs obtained from a concrete extracted with hexane: 0.0003% to 0.002%
Excipient: concentration adapted to obtain 100%

Composition No. 2:
Absolute of *Allium sativum* bulbs obtained from a concrete extracted with ethyl acetate: 0.0005% to 0.002%
Excipient: concentration adapted to obtain 100%

Composition No. 3:
Absolute of *Allium sativum* bulbs obtained from an oleoresin extracted with acetone: 0.0005% to 0.002%
Excipient: concentration adapted to obtain 100%.

A composition according to the invention is extremely simple and inexpensive.

The invention covers a preventive or curative cosmetic and/or therapeutic process for treating cellulite, localized dermal (and hypodermal) excess adipose, or obesity, wherein at least one extract of *Allium sativum* bulbs is applied topically as an antiadipose active agent to areas of skin to be treated. The invention also relates to a treatment process wherein a composition according to the invention is used.

The invention also relates to the use of at least one extract of *Allium sativum* bulbs as an antiadipose active agent for the preventive or curative cosmetic treatment, by topical application to areas of skin to be treated, of cellulite and of localized dermal excess adipose.

The invention also relates to the use of at least one extract of *Allium sativum* bulbs as an antiadipose active agent for the preparation of a therapeutic composition for the preventive or curative treatment, by topical application to areas of skin to be treated (abdomen, thighs, hips, buttocks, rolls, limbs, etc.), of obesity. The invention also relates to a process for preparing a therapeutic composition for the preventive and/or curative treatment, by topical application to areas of skin to be treated, of obesity, wherein an effective amount of at least one extract of *Allium sativum* bulbs is incorporated as antiadipose active agent into the composition.

Advantageously, in a process or the use according to the invention, an amount of at least one extract of *Allium sativum* bulbs which is suitable for causing at least substantially an inhibition of the differentiation of preadipocytes into mature adipocytes and/or for at least substantially limiting or inhibiting the hypertrophy of mature adipocytes, and which achieves this without causing any skin irritation or sensitization, is used.

The invention also covers a process for the extracorporal inhibition of the adipocytic conversion of preadipocytes into mature adipocytes, wherein an effective amount of at least one extract of *Allium sativum* bulbs is placed in contact with preadipocytes or a biological tissue incorporating them.

Advantageously, in a process or a use according to the invention, one or more nonaqueous extract(s) of *Allium sativum* bulbs is (are) used exclusively as antiadipose active agent(s).

Advantageously and according to the invention, between 3 ppm and 20 ppm of extract(s) of *Allium sativum* bulbs are used.

Advantageously and according to the invention, at least one essential oil and at least one emulsifier are used as antiadipose active agent. As a variant, advantageously and according to the invention, at least one absolute in aqueous solution is used as antiadipose active agent.

Advantageously and according to the invention, at least one extract of *Allium sativum* bulbs chosen from an essential oil; an absolute obtained from a concrete extracted with hexane; an absolute obtained from a concrete extracted with ethyl acetate; and an absolute obtained from an oleoresin extracted with acetone, is used as nonadipose active agent.

Advantageously, in a process or a use according to the invention, a composition according to the invention is used. The invention also relates more generally to a composition which is suitable for carrying out a (cosmetic and/or therapeutic) treatment process or an inhibition process according to the invention.

The invention also relates to a composition, a treatment process—especially a cosmetic process—, a process for preparing a therapeutic composition the use, which feature, in combination, all or some of the characteristics mentioned hereinabove or hereinbelow.

The efficacy of the invention emerges from the results of examples 1 to 4 described below and illustrated with reference to the attached figures.

Examples 1, 2, 3 and 4 illustrate the biological efficacy on the processes of adipocyte hyperplasia and hypertrophy of an essential oil of *Allium sativum* bulbs (referred to as EO); of an absolute of *Allium sativum* bulbs obtained from a concrete extracted with hexane (referred to as ACH); of an absolute of *Allium sativum* bulbs obtained from a concrete extracted with ethyl acetate (referred to as ACEA); and of an absolute of *Allium sativum* bulbs obtained from an oleoresin extracted with acetone (referred to as AOA). The methods for preparing the EO, ACH, ACEA and AOA solutions, the cellular models used and the treatment methods are detailed below.

Preparation of the EO, ACH, ACEA and AOA solutions
Preparations of the EO Solution:
An EO solution introduced into the culture medium is prepared by tenfold dilution in water for cell culture (Eurobio®, France) of a stock solution of the EO (sold by SIGMA-ALDRICH FINE CHEMICALS: Garlic oil, Chinese, ref. W250309) consisting of 18.4 $\mu$l of EO and 981.6 $\mu$l of Liposol (natural emulsifier based on substances extracted from plant cell membranes, sold by Siegen, Switzerland). A control solution introduced into the culture medium is prepared by tenfold dilution in water for cell culture (Eurobio®, France) of a control stock solution consisting of 18.4 $\mu$l of water for cell culture (Eurobio®, France) and 981.6 $\mu$l of Liposol.

Preparation of the aqueous solutions of ACH, ACEA and AOA absolutes:
The absolutes according to the invention are prepared according to a process, which as such, is classical, well known and well defined in perfumery.

Briefly, an absolute is an extract obtained from at least two extraction steps. A first extraction step is realized with a nonaqueous volatile extraction solvent—especially non benzenic—and allows to obtain a concrete, when the starting plant matter is fresh or defrosted (after being frozen for its preserving), or an oleoresin when the starting plant material is in a dry state. The second extraction step is realized with ethanol as solvent.

To obtain an ACH absolute, fresh garlic cloves are peeled, then mechanically grinded. A first extraction step with hexane is realized. By moderate heating, without boiling the solution, and after a complete evaporation of hexane, the concrete is collected. The latter contains waxes and aromatic compounds. At ambient temperature, it shows a pasty and yellow aspect.

After dissolution of this concrete in ethanol, the solution is fittered then frozen at −10° C., to eliminate waxes. After distillation of ethanol, the ACH absolute is obtained. Diluated at 25% in ethanol, it is a clear yellow limpid solution with a strong odor.

The ACAE absolute is prepared by following a process very closed to the one used for the ACH absolute. The first extraction step, this time, consists of an extraction with ethyl acetate. The ACAE absolute, diluted at 25% in ethanol, is a clear brown solution with a moderate odor.

The AOA absolute is prepared by following a process very closed to the one used for the ACH absolute as well. This time, the first extraction step is realized from dry garlic cloves and with acetone. At the end of this first extraction step, an oleoresin is obtained. At ambient temperature, it is in the form of a very dark brown paste. Then, this one is distilled with ethanol to finally obtain the AOA absolute, a brown limpid solution with a weak odor.

The ACH, ACEA and AOA solutions introduced into the culture medium are prepared by tenfold dilution in water for cell culture (Eurobio®, France) of stock solutions of each absolute (ACH, ACEA or AOA) consisting of 18.4 µl of the absolute (ACH, ACEA or AOA) and 981.6 µl of water for cell culture (Eurobio®, France).

Cell Models Used:

The mechanisms involved in the process of adipocyte differentiation have been studied in vitro for many years (general review: Klaus S., BioEssays, 19: 215–223, 1997).

The biological activities of EO, ACH, ACEA and AOA are demonstrated using cultures of 3T3-F442A cells (cell line of murine origin, used for its capacity to accumulate lipids) and then confirmed on primary cultures of human preadipocytes.

The cells are inoculated in 6-well plates (inoculation density: 15 000 cells/well) and maintained to the point of confluence in DMEM medium-10% DCS plus antibiotics. At confluence, the preadipocytes are then cultured in DMEM medium-10% FCS plus insulin. The treated cells are maintained in the culture medium, to which are finally added 25 µl of one of the test solutions (EO, ACH, ACEA or AOA) per millilitre of culture medium. The control 3T3-F442A preadipocytes are cultured in the culture medium, to which are added 25 µl of control solution per millilitre of culture medium. The culture medium is renewed every 48 hours.

Human Preadipocyte Primary Cultures:

The human preadipocytes (ZenBio®, USA) are cultured in accordance with the supplier's instructions. On receipt, the human preadipocytes are cultured in the adequate medium supplied, to which are finally added from 3 µl to 10 µl of one of the test solutions (EO, ACH, ACEA or AOA) per millilitre of culture medium. The control preadipocytes are maintained in culture in the medium alone. The culture medium is renewed every 3 days.

EXAMPLE 1

Effect of the EO, ACH, ACEA or AOA Solutions on Adipocyte Morphology (FIGS. 1A to 1F)

Figure 1A:
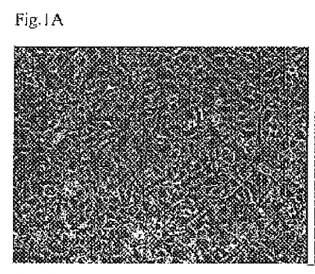
FIGS. 1A to 1F, 2A and 2B are microscopic photographic views of adipocytes.
Figure 1B:
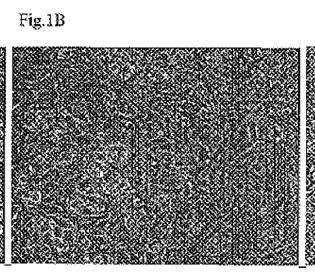
Figure 1C:
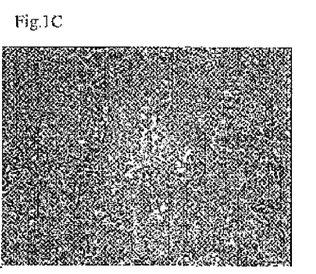
Figure 1D:
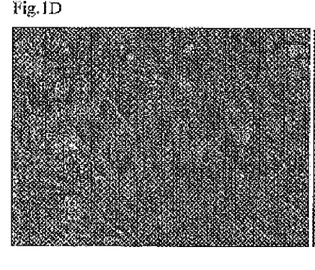
Figure 1E:
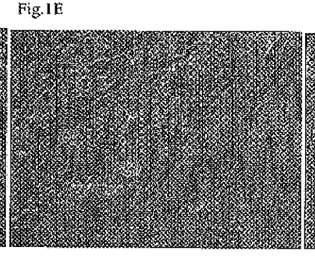
Figure 1F:
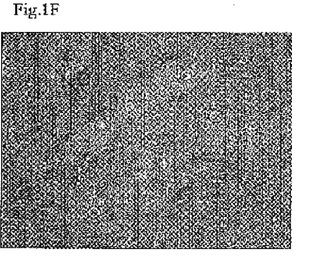

After 7 days (3T3-F442A cells) and 9 days (human preadipocytes) of treatment, the effect of the EO, ACH, ACEA and AOA solutions on the differentiation process was studied on the basis of morphological criteria, by observation by microscopy of the treated cultures and of the control cultures. The cells are considered as differentiated by morphological analysis by reverse-phase microscopy coupled to a CCD camera, when they acquire a round contour, and when their cytoplasm is totally filled with lipid droplets. It is found that the EO, ACH, ACEA or AOA solutions inhibit the cellular differentiation of murine 3T3-F442A preadipocytes (FIGS. 1A to 1C).

After 7 days of chronic treatment, the EO solution (FIG. 1A) or ACH solution (FIG. 1B) induces a significant decrease in the number of mature adipocytes developed. Most of the cells maintain their preadipocytic fibroblast morphology, with a very marked inhibition in lipid accumulation. Although not shown in the figures, the same results are obtained with the ACEA and AOA solutions. The control 3T3-F442A cells (FIG. 1C) follow the normal process of terminal differentiation and acquire the morphological characteristics of mature adipocytes, with a cytoplasm filled with droplets of triglycerides, as evidenced by the strong refringence.

It is also found that the EO, ACH, ACEA or AOA solutions inhibit the process of terminal differentiation of human preadipocytes.

The human preadipocytes cultured in the presence of an EO solution (FIG. 1D) or an ACH solution (FIG. 1E) maintain a preadipocytic morphology: the human cells remain fusiform with very few detectable intracytoplasmic lipid droplets. Although not shown in the figures, the same results are obtained with the ACEA and AOA solutions. In comparison, the control human preadipocytes (FIG. 1F) lose their fibroblast morphology, with the appearance of a spherical shape and the existence of numerous intracytoplasmic lipid vesicles that are identifiable by their strong refringence.

The chronic treatment with essential oil of *Allium sativum* bulbs (EO), the absolute of *Allium sativum* bulbs obtained from a concrete extracted with hexane (ACH), the absolute of *Allium sativum* bulbs obtained from a concrete extracted with ethyl acetate (ACEA) or the absolute of *Allium sativum* bulbs obtained from an oleoresin extracted with acetone (AOA) limits the morphological and biochemical changes characteristic of adipocyte differentiation. On contact with EO, ACH, ACEA and AOA, the preadipocytes are no longer sensitive to the hormonal environment which regulates their lipid metabolism and which normally allows the conversion of the preadipocytes into mature differentiated adipose cells.

EXAMPLE 2

Figure 2A:
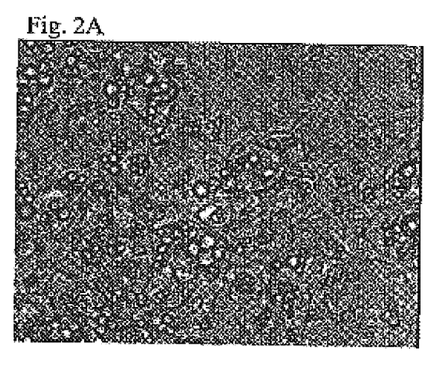
Figure 2B:
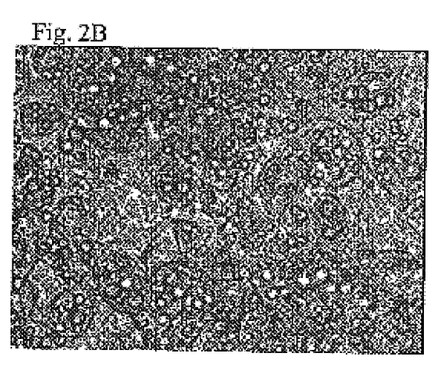

Effect of the EO, ACH, ACEA or AOA Solutions on the Morphology of Mature Hypertrophied Adipocytes (FIGS. 2A and 2B)

At confluence, the 3T3-F442A preadipocytes are cultured for 4 days in differentiating medium (DMEM-10% FCS plus insulin). Under these conditions, the cells pass to the "mature adipocyte" stage, in which the volume and the content of triglycerides has been increased. The cells are then treated as previously.

In comparison with the control mature adipocytes (FIG. 2B), which have a voluminous spherical shape and a large accumulation of intracytoplasmic lipid vesicles, the mature adipocytes treated with an EO solution (FIG. 2A) have a less rounded cellular morphology and a greatly reduced content of intraadipocytic lipid vesicles, such that the EO solution according to the invention is found to be effective in the process for limiting adipocyte hypertrophy, by reversing the differentiation process. The same results are obtained with the ACH, ACEA or AOA solutions according to the invention.

EXAMPLE 3

Figure 3A:
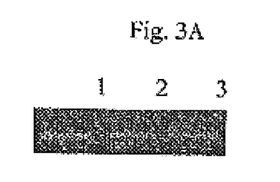
FIGS. 3A and 3B are photographic views of electrophoresis gels.
Figure 3B:
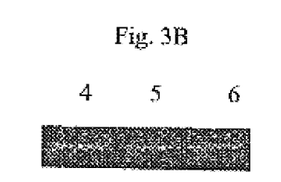

Effect of the EO, ACH, ACEA or AOA Solutions on the Expression of PPARγ2 mRNA (FIGS. 3A and 3B)

Adipocyte differentiation is an important feature of the development of adipose tissue and obesity. The adipocyte differentiation process is characterized in vitro by the programmed induction of various genes regulating lipoprotein lipolysis, fatty acid capture by cells, and fatty acid and triglyceride synthesis. These genes can be schematically categorized as differentiation markers that are: very early (such as expression of mRNA of the lipoprotein lipase), early (such as PPARγ12 mRNA expression), or late (such as leptin expression) (general review: Morrison R. F., Farmer S. R., J. Cell. Biochem. Suppl. 32/33: 59–67, 1999). The degree of differentiation of the adipocyte can thus be precisely established by studying the level of expression of the appropriate markers like PPARγ2 mRNA or leptin.

The family of nuclear receptors of PPAR ("Peroxisomal Proliferator-Activated Receptor") type consists of 3 subtypes: PPARα, PPARδ, PPARγ. PPARα is strongly expressed in the liver, where it regulates the expression of the genes involved in lipid metabolism. PPARγ is expressed ubiquitously; the function of this receptor still remains to be determined. PPARγ exists in the form of two isoforms, PPARγ1 and PPARγ2. It is PPARγ2 which is strongly expressed in mammalian adipose tissue. When PPARγ2 is activated, it induces the transcription of several adipocyte genes encoding proteins and enzymes involved in the creation and maintenance of the adipocyte phenotype. It thus plays a fundamental role in the differentiation and metabolism of adipose cells.

The effect of the EO, ACH, ACEA or AOA solutions on the expression of PPARγ2 mRNA was determined after 3 days (FIG. 3A, 3T3-F442A cells) or 6 days (FIG. 3B, human preadipocytes) of treatment. The PPARγ2 mRNA content is analyzed by RT-PCR ("Reverse Transcription-Polymerase Chain Reaction"), after having first; purified the RNA in accordance with the procedure of the RNeasy Total RNA System kit (Qiagen®), quantified the RNA content of the samples by the measurement and the ratio of the absorbences at 260 and 280 nm, and checked, after migration on agarose gel, the quality of the RNAs obtained.

For the RT step, the complementary DNA (cDNA) is synthesized from 1 μg of total RNA (3T3-F442A) or 0.2 μg of total RNA (human preadipocytes). The amplifications of the cDNA encoding PPARγ2 are obtained in the presence of the appropriate Sense and Antisense primers (Genset®, cf. table 1). The sizes of the PCR products are 307 base pairs (3T3-F442A cells) and 582 base pairs (human preadipocytes). The appropriate controls (reverse transcription and PCR amplification steps) were performed. The PCR mixtures were subjected to 22 cycles (3T3-F442A cells) or 35 cycles (human preadipocytes) of amplification by denaturing (2 minutes at 94° C.), hybridization (1 minute at 60° C.) and elongation (6 minutes at 72° C.). The PCR products are analyzed by agarose gel electrophoresis and visualized with ethidium bromide.

The sense strand for murine PPARγ2 is SEQ ID NO 1 (5'-TGTTGACCCAGAGCATGGTGCCT-3'). The antisense strand for murine PPARγ2 is SEQ ID NO 2 (5'-CAGGTTCTACTTTGATCGCACTT-3'). The sense strand for human PPARγ2 is SEQ ID NO 3 (5'-GCGATTCCTTCACTGATAC-3'). The antisense strand for human PPARγ2 is SEQ ID NO 4 (5'-GCATTATGAGACATCCCCAC-3').

TABLE 1

|  | Murine PPARγ2 | Human PPARγ2 |
| --- | --- | --- |
| Sense | 5'-TGTTGACCCAGAGCATGGTGCCT-3' | 5'-GCGATTCCTTCACTGATAC-3' |
| Antisense | 5'-CAGGTTCTACTTTGATCGCACTT-3' | 5'-GCATTATGAGACATCCCCAC-3' |

The level of expression of the PPARγ2 adipogenic transcription factor is greatly reduced when the 3T3-F442A cells have been in contact with an EO solution (FIG. 3A, result 2) or an ACH solution (FIG. 3A, result 3), in comparison with the control cells, as is evidenced by the intensity of the band (FIG. 3A, result 1). The same results are obtained with the ACEA solution and the AOA solution.

Similarly, the EO, ACH, ACEA or AOA solutions according to the invention significantly inhibit the expression of the PPARγ2 mRNA of the human preadipocytes (FIG. 3B, result 5 illustrating a treatment with an EO solution, and result 6 illustrating a treatment with an ACH solution), in comparison with the control human preadipocytes (FIG. 3B, result 4).

The essential oil of *Allium sativum* bulbs (EO), the absolute of *Allium sativum* bulbs obtained from a concrete extracted with hexane (ACH), the absolute of; *Allium sati* vum bulbs obtained from a concrete extracted with ethyl acetate (ACEA) and the absolute of *Allium sativum* bulbs obtained from an oleoresin extracted with acetone (AOA) act on the differentiation program by reducing the expression of the PPARγ2 messenger.

EXAMPLE 4

Effect of EO, ACH, ACAE and AOA on Leptin Secretion

The capacity of EO, ACH, ACAE or AOA solutions to inhibit the differentiation process in human preadipocytes was determined by measuring the amount of leptin secreted into the culture media in various tests. Leptin, coded for by the ob gene and synthesized and secreted by the adipocytes, is considered to be a late marker of the adipocyte differentiation process. In vitro, the basal secretion of leptin increases progressively throughout the conversion of preadipocytes to mature adipocytes (MacDougald, O. A. et al., Proc Natl Acad Sci, USA, 92: 9034–9037, 1995).

The effect of EO, ACH, ACAE and AOA solutions on leptin secretion was studied over a treatment period of 9 days (human preadipocytes), which is an appropriate time for a study of the specific components of the differentiation process. The amounts of leptin secreted by the control cells and the treated cells were measured in the culture medium, which was sampled at days 3, 6 and 9 (days when the medium was renewed). The quantity of leptin released was determined using an ELISA assay (R&D Systems Europe), according to the manufacturer's instructions. The results were expressed as the mean±s.e.m. Statistical comparisons were made through a Student's T test ($p<0.05$ being considered as significant).

The results were normalized as follows. After nine days of treatment, the leptin values measured on the third, sixth and ninth days were added together for each of the treatments and expressed as a percentage of the values obtained for the controls (Table 2).

TABLE 2

Effect of EO, ACH, ACAE or AOA solutions on leptin secretion

| Treatment | Concentration | Leptin (% of control values) | | Significance |
| --- | --- | --- | --- | --- |
| | | Mean | s.e.m. | |
| EO | 14 ppm | 69.7 | 2.7 | P < 0.001 |
| ACH | 3 ppm | 69.4 | 4.4 | P < 0.01 |
| ACH | 10 ppm | 36.3 | 0.1 | P < 0.001 |
| ACAE | 10 ppm | 81.7 | 2.1 | P < 0.01 |
| AOA | 10 ppm | 80.9 | 2.1 | P < 0.001 |

The human preadipocytes cultured in presence of EO, ACH, ACAE and AOA secreted significantly smaller quantities of leptin into the culture medium than the amounts detected in the culture medium of non-treated human preadipocytes. The results obtained show that EO, ACH, ACAE and AOA solutions act within the differentiation programme and are able to inhibit the adipocyte conversion process.

What is claimed is:

1. A method of treating cellulite in a patient in need of treatment thereof, comprising:

topically administering to said patient an effective amount of an extract of *Allium sativum* to areas of the skin of said patient to be treated, and wherein between 3 ppm and 20 ppm of extract of *Allium sativum* is present in the topically administered composition.

2. The method according to claim 1, wherein said extract is a non-aqueous extract.

3. A method of treating cellulite in a patient in need of treatment thereof, comprising:

topically administering an effective amount of a composition to said patient, wherein said composition comprises an extract of *Allium sativum* bulbs, and wherein said extract is selected from the group consisting of an essential oil, an absolute obtained from a concrete extracted with ethyl acetate, and an absolute obtained from an olio resin extracted with acetone, and wherein between 3 ppm and 20 ppm of extract of *Allium sativum* is present in the topically administered composition.

* * * * *